United States Patent [19]

Champion et al.

[11] Patent Number: 4,850,993

[45] Date of Patent: Jul. 25, 1989

[54] BLOOD BAG SYSTEM INCORPORATING QUINOLONE CARBOXYLIC, ACID DERIVATIVES

[75] Inventors: Alexander B. Champion, Albany; Michael S. Collins, Pinole, both of Calif.

[73] Assignee: Miles Laboratories, Inc., Elkhart, Ind.

[21] Appl. No.: 944,061

[22] Filed: Dec. 22, 1986

[51] Int. Cl.$^4$ .............................................. A61B 19/00
[52] U.S. Cl. .................................... 604/408; 604/403
[58] Field of Search ..................................... 604/4–6, 604/403, 408, 410–416

[56] References Cited

U.S. PATENT DOCUMENTS 4,014,329  3/1977  Welch et al. ............................ 604/4
4,484,920  11/1984  Kaufman et al. ...................... 604/87
4,639,458  1/1987  Katdare ................................ 514/311

Primary Examiner—C. Fred Rosenbaum
Assistant Examiner—Mark F. Colosimo
Attorney, Agent, or Firm—James A. Giblin; Pamela A. Simonton

[57] ABSTRACT

A method and system is disclosed for introducing antibacterial agents, for example, quinolone carboxylic acid derivatives into blood bag systems for preventing massive bacteria growth in stored blood and blood components. The quinolone carboxylic acid derivative can be added to a collection container before, during or after the collection of blood and blood components. The addition of a quinolone carboxylic acid derivative to blood bag systems allows for increase in storage time for blood and blood components without the threat of massive bacterial contamination.

11 Claims, 2 Drawing Sheets

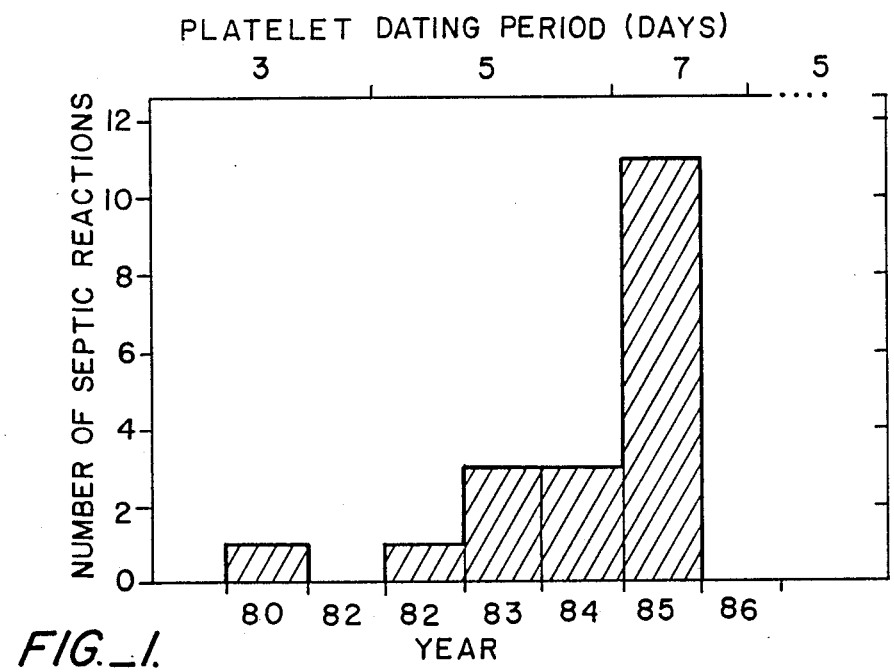
FIG._1.
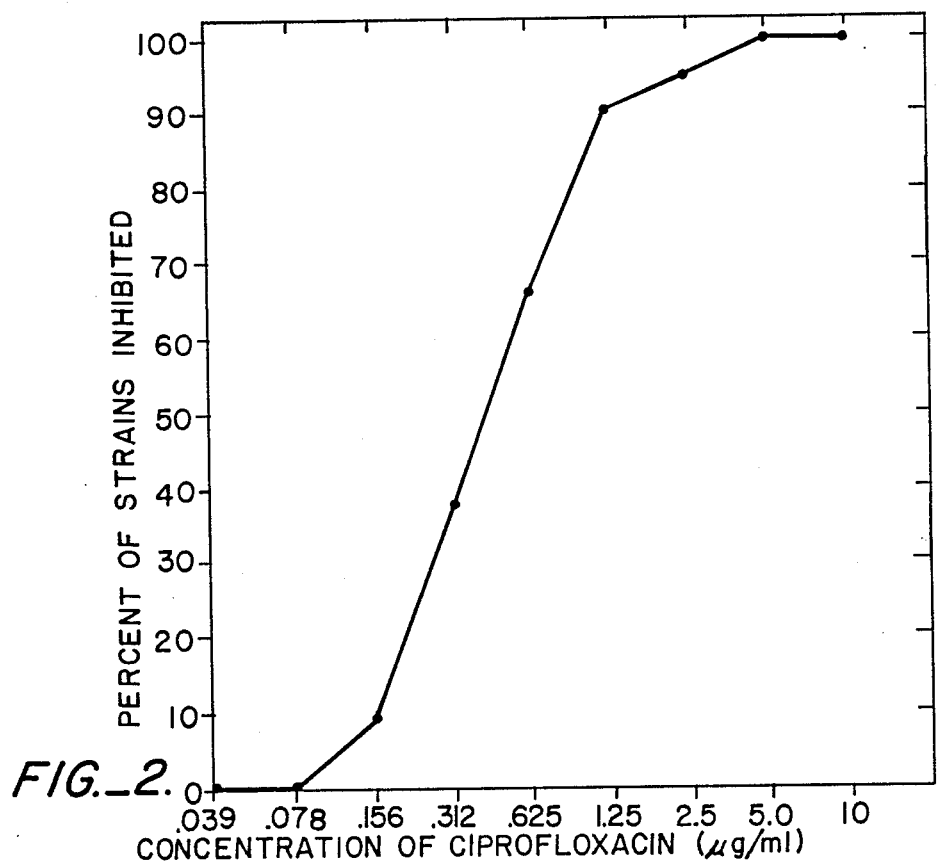
FIG._2.

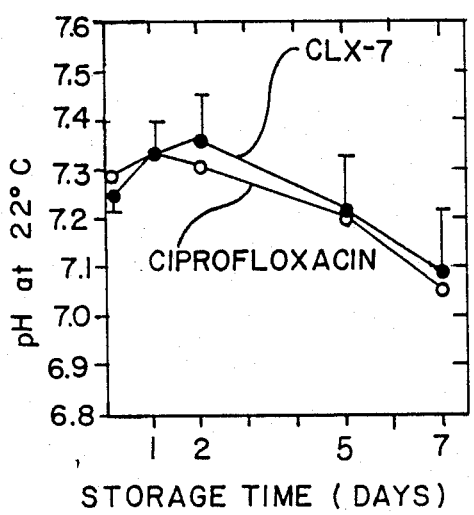
FIG._3a.
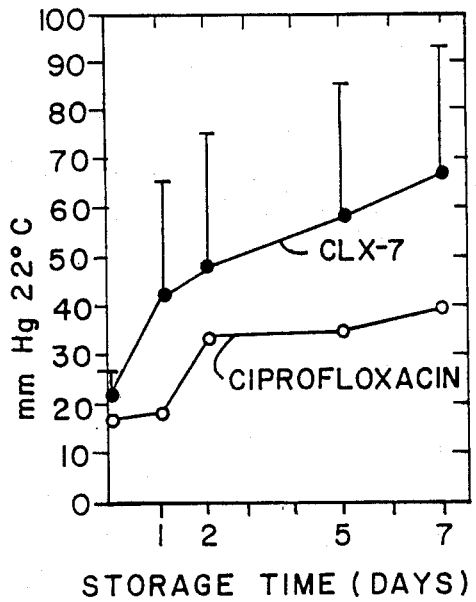
FIG._3b.
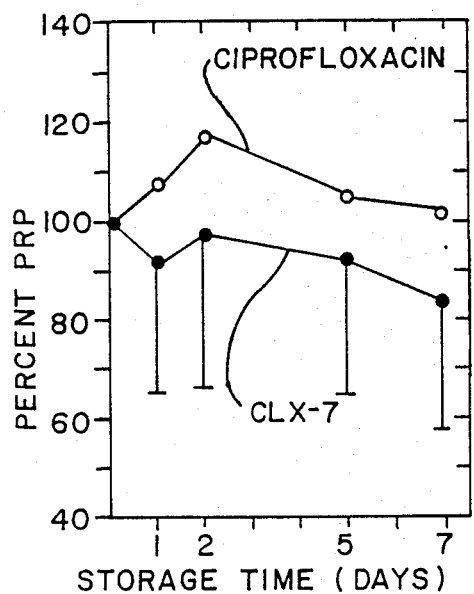
FIG._3c.
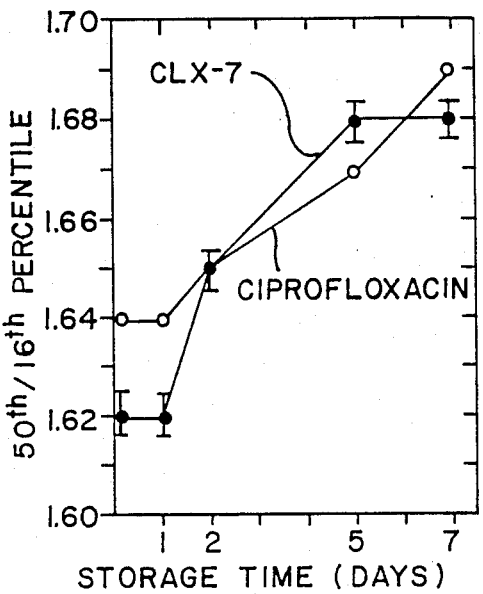
FIG._3d.

BLOOD BAG SYSTEM INCORPORATING QUINOLONE CARBOXYLIC, ACID DERIVATIVES

BACKGROUND OF THE INVENTION

1. Field of the Invention

This invention relates to the storage of blood and blood components. It has among its objects a novel system and method of storing blood and blood components in the presence of antibacterial agents to prevent massive bacterial contamination. A specific group of such antibacterial agents include quinolone carboxylic acid derivatives.

2. Description of the Prior Art

Proliferation of inadvertently introduced bacteria into blood and blood component collection and storage systems is a rare event. Additional contamination is thought to occur most likely at the time of phlebotomy. But the consequences of bacterial contamination of blood and blood components can result in a potentially life threatening condition.

Refrigeration of collected blood and blood components and short term storage have been found to minimize the incidence of massive bacterial contamination. Shortening the storage period often results in the disposal of a large number of units of blood and blood components that are not contaminated. This results in a loss of an important and often critical supply of blood and blood products. In addition, some blood components, such as platelets stored as platelet-rich plasma and platelet concentrates (PC) possess a better in vivo half-life when prepared and stored at ambient temperature. With the introduction of blood bag systems which include film that allow for greater gas transmissibility, platelets have been stored for periods of up to 7 days. When the storage period was increased to 7 days the incidence of contamination of stored platelets increased prompting the FDA to decrease platelet storage from up to 7 days to up to 5 days. See FIG. 1 showing an increase in the incidence of contaminatin since the end of 1984.

SUMMARY OF THE INVENTION

The invention described herein is a method and system for preventing massive bacterial contamination in collected and stored blood and blood component products by introducing an antibacterial agent into the collection and storage containers. In the present method and systems, anti-bacterial agents, such as quinolone carboxylic acid derivatives can be introduced into the blood bag system before, during or shortly after collection.

The primary advantage of the present invention is preventing massive bacterial contamination when blood and blood components are stored at room temperature or inadvertently not timely refrigerated.

Another advantage of the invention is to increase the storage time of blood and blood components.

Yet another advantage of the invention is to increase the storage time of platelets at ambient temperature to greater than 7 days. This would provide a safer platelet transfusion product by preventing massive bacterial growth in platelets that are accidently contaminated.

BRIEF DESCRIPTION OF THE DRAWINGS

FIG. 1 is a graph of the number of septic reactions/year from platelet infusions.

FIG. 2 is a graph of the distribution of minimum inhibitory concentrations for ciprofloxacin.

FIG. 3 is a series of graphs of ciprofloxacin platelet data compared with historical data.

DESCRIPTION OF THE PREFERRED EMBODIMENTS

In a preferred embodiment the quinolone carboxylic derivative is a fluoro-quinolone which is a subset of a general family of quinolones. Examples of quinolones and their manufacturer include ciprofloxacin by Miles, ofloxacin by Hoeschst, norfloxacin by Merck, Sharpe and Dohme, and enoxacin by Warner-Lambert.

Quinolones, such as ciprofloxacin, act by inhibiting the bacterial enzyme DNA gyrase. Bacterial DNA is a double stranded circle in which the two strands are wrapped around each other in a helical fashion. DNA replication is initiated at one point on the circle. The strands are first pulled apart at the initiation point (to allow the sequence to be read). This causes the number of twists per unit length to increase on both sides of the initiation point. DNA gyrase decreases the twist density and thus allows the continual unravelling of the entire double stranded circle. Without DNA gyrase, DNA replication is not possible, and therefore bacterial replication cannot occur.

Ciprofloxacin also has other less understood actions that will kill bacteria when added at levels higher than the amount needed to inhibit bacterial replication.

Ciprofloxacin is a broad spectrum antibacterial agent, affecting both gram negative and gram positive bacteria. It is effective at low concentrations e.g. 5 $\mu$g/ml. It is autoclavable and stable in plasma at room temperature for 7 days. It is not toxic to humans by the intravenous (IV) route at levels (100–200 mg) that are 50 to 100 times the dose that would be received in a transfusion of eight 50 ml PC each containing 5 $\mu$g/ml ciprofloxacin.

Experiments to Show the Effectiveness of Ciprofloxacin

There are a number of published reports showing the effectiveness of ciprofloxacin e.g. Wolfson JS and Hooper DC. The Fluoro-quinolones: Structures, Mechanisms of action and Resistance, and Spectra of Activity in vitro. Antimicrob. Agents Chemother. 28: 581–6 (1985).

A number of experiments to confirm ciprofloxacin's effectiveness has been performed. Nineteen different organisms were isolated from skin at the phlebotomy site from 11 individuals representing multiple nationalities and races (Chinese, black, white, Korean). Sterile Q-tips were dipped in sterile saline and rubbed vigorously at the phlebotomy site. The entire surface of an agar plate containing an all purpose growth medium (5% sheep blood trypticase soy agar) was rubbed with the Q-tips. The plates were incubated for 2 days at 37° C. One to 3 different colony types were found per plate. Representatives of each colony type were subcultured at 22° C. to select for organisms that would grow at the temperature in which platelets would be stored. Further culturing was done to yield pure strains. The strains were characterized by morphology, gram stains, growth on mannitol salt agar, ability to grow anaerobically on glucose, and the coagulase test. All strains were gram positive cocci and appeared singly or in clusters. Four were identified as Micrococcus by their inability to grow anaerobically on glucose. Fourteen strains were identified as staphylococci by their ability to show good growth anaerobically on glucose. One strain remained unidentified at the group level by showing only weak growth on glucose anaerobically. Three strains were identified tentatively as *Staphylococcus aureus* by a coagulase positive result, although the results were tentative and conflicted with the results of growth on a mannitol salt medium.

For each of the 19 human strains the minimum concentration of ciprofloxacin to completely inhibit growth (MIC in µg/ml) was determined. Also included were *S. aureus* ATCC 14514, and *S. epidermidis* QA. The MIC tests were performed on agar plates containing Mueller-Hinton medium. A series of plates were made containing ciprofloxacin in the medium. The range of concentration varied 2 fold from 10 µg/ml to 0.038 µg/ml. On each plate in a known spot (usually 9 to 10 strains per plate), 50,000 colony forming units (CFU) in 5 µl were added. The experiment was run in duplicate. The plates were incubated overnight at 37° C. The MIC is defined as the concentration of ciprofloxacin in which no growth is observed. The results for the 19 human isolates and 2 reference strains of gram positive cocci are shown in Table 1 and in FIG. 2.

The MICs for a number of other gram positive and gram negative organisms has been determined. These bacteria included examples of the organisms implicated in cases of bacterial sepsis (p. I 157 of the transcript of the Blood Product Advisory Committee meeting held 2/13/86).

TABLE 1

|  |  | MIC µg/ml Ciprofloxacin |
|---|---|---|
| 11 | Staphylococcus (coagulase negative) | 0.157–0.625 |
|  | S. epidermidis(QA) | 2.5 |
| 3 | S. aureus | 0.625 |
|  | S. aureusATCC14504 | 1.25 |
| 4 | Micrococcus | 1.25–5.0 |
| 1 | gram positive coccus | 1.25 |
|  | mean | 0.94 µg/ml |

TABLE 2

Reference Strains of Gram Negative Bacilli

| Species | Strain | MIC (µg/ml) Ciprofloxacin |
|---|---|---|
| Pseudomonas aeruginosa* | FDG 5 ATCC27316 | 0.625 |
| Salmonella typhimurium | SL1027 |  |
| Serratia marcescens | 435 | 0.313 |
|  | 436 |  |
|  | 437 |  |
| Klebsiella pneumoniae | ATCC8047 |  |
|  | ATCC10031 | 0.156 |
|  | 2CD |  |
| Serratia marcescens | 438 | 0.078 |

*Brain heart infusion medium, all others on Mueller-Hinton medium

TABLE 3

Reference Strains of Gram Positive Cocci

| Species | Strain | MIC (µg/ml) Ciprofloxacin* |
|---|---|---|
| Enterococcus | 101 | 2.5 |
| Enterococcus | 102 | 1.25 |
|  | 103 |  |
|  | 104 |  |
|  | 105 |  |
|  | 106 |  |
|  | 107 |  |
| S epidermidis |  | 1.25 |

TABLE 3-continued

Reference Strains of Gram Positive Cocci

| Species | Strain | MIC (µg/ml) Ciprofloxacin* |
|---|---|---|
| (Q.A. strain) |  |  |

*In brain heart infusion medium

Platelet Storage Studies with Ciprofloxacin

It has been established that PC inoculated with small numbers of *S. epidermidis* will contain massive numbers of bacteria in a few days. In our own experiments we inoculated PC stored for 1 day with 5 cfu (n=8) or 20 cfu (n=8) of *s. epidermidis* (Q.A. strain). Massive growth (>$10^7$ CFU/ml) was seen within 3 to 4 days after inoculation (7 of 8 PC and 4 of 8 PC, respectively).

To test the effectiveness of ciprofloxacinin stored platelet concentrates the following pair study was done. Two units of blood were drawn from ABO compatible donors. Platelet-enriched plasma (RPR) was prepared by centrifugation at 2900 RPM for 126 seconds. A PRP pool was made, sampled for in vitro platelet assays, and then split evenly into two CLX-7 satellite bags. Platelet concentrates were made by centrifugation at 3700 RPM for 6 min in an IEC PR6000 floor model centrifuge. All but 50–55 ml of plasma was removed from the platelet pellet. After a 90 minute rest period the bags were placed on a horizontal agitator (70 cycles/min). After 30 minutes on the shaker, when the platelets were nearly all resuspended, each member of the pair received 10,000 cfu of *S. epidermidis* (n=2) or 10,000 cfu of *S. aureus* ATCC 14504 (n=2). These two species are the ones most often implicated in contaminated PC. One member of the pair received enough (250 µg/ml) ciprofloxacin to make the final concentration 5 µg/ml. The bags were returned to the shaker and stored for 7 days at 22° C. The PRP and PC at days 1, 2, 5 and 7 were sampled for the following in vitro assays: pH, $PO_2$, the platelet concentration (count), recovery from hypotonic stress, and the sizing parameters, geometric standard deviation and the mean volume. Note that the size of the inoculum was 500 to 10,000 times greater than the inoculum needed to get massive bacterial growth in most PC.

Results

As to be expected there was massive growth by day 2 in those units not receiving ciprofloxacin (1.4 to $8.0 \times 10^7$ CFU/ml). In the 4 PC receiving 5 µg/ml ciprofloxacin, no viable bacteria were recovered during storage (0 CPU/ml on days 1, 2, 5 and 7).

The results of the in vitro assays for the PC receiving ciprofloxacin were averaged and compared with historical data (n=21) in CLX-7 (see FIG. 3). The ciprofloxacin platelet data was comparable to historical data. The ciprofloxacin $PO_2$ is lower than historical because the platelet concentration (count) was unusually high. We have seen counts as low as 600,000/µl to as high as 2,600,000/µl. From other studies we have found that high $PO_2$ affects adversely the hypotonic stress assay which is consistent with the results found here.

Under blood banking conditions, addition of ciprofloxacin to PC at low concentrations killed hugh inocula of the two common skin organisms (*S. aureus* and *S. epidermidis*) most often implicated in contaminated PC.

In vitro platelet parameters were not affected by the presence of ciprofloxacin.

Numerous existing blood bag systems could be adapted to include the presence or addition of a quinolone carboxylic acid derivative such as ciprofloxacin. For example U.S. Pat. No. 4,484,920 shows a container for mixing a liquid and a solid initially placed in separate compartments. The blood or blood component would be the liquid, the quinolone carboxylic acid derivatives could be in a separate compartment as either a solid, such as a powder or pellet formulation, or as a liquid.

One method of introducing an appropriate amount of a quinolone carboxylic acid derivative is to include the quinolone in a satellite bag which is attached to at least one of the main blood bags. The quinolone could be in liquid, power or pill formulation. One embodiment would be to provide an appropriate amount of quinolone, for example 250 $\mu$g of ciprofloxacin in a pill formulation. The pill formulation could be introduced into the blood bag system by activating an opening and allowing the quinolone to be admixed with the blood or blood components. The quinolone could be dissolved or flushed from the satellite pouch by introducing the blood or blood components into the satellite bag and then allowing the blood or blood components to be returned to the main blood bag. Alternatively, the appropriate amount of quinolone or other antibacterial agent would be in a liquid formulation.

The introduction of an antibacterial agent into a blood bag storage or collection system serves to destroy or supress the growth or reproduction of bacteria. Quinolone carboxylic acid derivatives have provided the above function without negatively affecting the viability of the blood or blood components. Other yet to be developed quinolones are deemed to be within the scope of this invention, as are other antibacterial agents that provide the desired function.

Given the above disclosure, it is thought variations will occur to those skilled in the art. Accordingly, it is intended that the above example should be construed as illustrative and the scope of the invention should be limited only by the following claims.

What is claimed is:

1. A method for reducing the likelihood of bacterial contamination in stored platelets comprising the steps of:
    (a) withdrawing blood from a donor;
    (b) collecting platelets from the blood into a collection container; and
    (c) storing the platelets;
    (d) wherein the improvement comprises admixing the platelets with a sufficient amount of an antibacterial agent to inhibit the growth of gram negative organisms and gram positive organisms during the storage of step (c).

2. The method of claim 1 wherein said antibacterial agent is a quinolone carboxylic acid derivative.

3. The method of claim 2 wherein said quinolone carboxylic acid derivative is selected from the group consisting of ciprofloxacin, ofloxacin, norfloxacin and enoxacin.

4. The method of claim 3 wherein said quinolone carboxylic acid derivative is ciprofloxacin.

5. The method of claim 4 wherein the ciprofloxacin is present in a final concentration of about 1 $\mu$g/ml to about 20 $\mu$g/ml.

6. The method of claim 5 wherein the final concentrate of ciprofloxacin is about 5 $\mu$g/ml.

7. The method of claim 1 wherein said antibacterial agent is placed in a separate but potentially communicating satellite compartment attached to said collection container.

8. The method of claim 1 wherein said anti-bacterial agent is in a liquid formulation.

9. The method of claim 1 wherein said anti-bacterial agent is in a dry formulation.

10. The method of claim 8 wherein said antibacterial agent is a quinolone selected from the group consisting of ciprofloxacin, ofloxacin, norfloxacin and enoxacin.

11. The method of claim 9 wherein said antibacterial agent is a quinolone selected from the group consisting of ciprofloxacin, ofloxacin, norfloxacin and enoxacin.

* * * * *